United States Patent
Linder et al.

(10) Patent No.: US 9,428,810 B2
(45) Date of Patent: Aug. 30, 2016

(54) DETECTION OF A TARGET IN A PRESERVATIVE SOLUTION

(75) Inventors: James Linder, Omaha, NE (US);
Menashi Cohenford, Huntington, WV (US); Erin Coffman, Nashua, NH (US); Brian B. Lentrichia, Acton, MA (US); Henrik Stender, Gentofte (DK); Kenneth Oliveira, Sudbury, MA (US)

(73) Assignee: Hologic, Inc., Marlborough, MA (US)

( * ) Notice: Subject to any disclaimer, the term of this patent is extended or adjusted under 35 U.S.C. 154(b) by 1123 days.

(21) Appl. No.: 12/408,179

(22) Filed: Mar. 20, 2009

(65) Prior Publication Data
US 2009/0233269 A1    Sep. 17, 2009

Related U.S. Application Data

(63) Continuation of application No. 10/618,443, filed on Jul. 11, 2003, now abandoned, which is a continuation-in-part of application No. 09/825,482, filed on Apr. 3, 2001, now abandoned.

(60) Provisional application No. 60/194,304, filed on Apr. 3, 2000, provisional application No. 60/225,524, filed on Aug. 15, 2000.

(51) Int. Cl.
  *C12Q 1/68*    (2006.01)
  *C12Q 1/70*    (2006.01)

(52) U.S. Cl.
  CPC ........... *C12Q 1/6881* (2013.01); *C12Q 1/6841* (2013.01); *C12Q 1/6888* (2013.01); *C12Q 1/708* (2013.01)

(58) Field of Classification Search
  None
  See application file for complete search history.

(56) References Cited

U.S. PATENT DOCUMENTS

| 6,280,946 B2 * | 8/2001 | Hyldig-Nielsen et al. ....... 435/6 |
| 6,969,585 B2 * | 11/2005 | Lorincz et al. .................. 435/6 |
| 2003/0108866 A1 * | 6/2003 | Cohenford et al. ............. 435/5 |

FOREIGN PATENT DOCUMENTS

WO    WO9310263    *    5/1993    ............... C12Q 1/68

OTHER PUBLICATIONS

Einsele et al. (J. Clin. Micro, 1997, 35(6):1353-1360).*

* cited by examiner

*Primary Examiner* — Stephanie K Mummert
(74) *Attorney, Agent, or Firm* — Hologic, Inc.

(57) ABSTRACT

This invention relates to methods, articles and compositions useful in detecting target substances in an alcoholic preservative solution, and for identifying sensors useful for binding to such targets. The methods allow for the simultaneous performance of sufficient fixation of a sample and binding of a detectable sensor to a target of interest in the sample. In one aspect, a method is provided that comprises contacting a sample suspected of containing a target with a detectable sensor molecule known to bind to such target in an alcoholic preservative solution. The method maybe performed in multiplex form to permit simultaneous analysis of a plurality of targets. Methods for identifying a sensor capable of binding to a desired target in an alcoholic preservative solution are also provided. An alcoholic preservative solution comprising one or more such detectable sensors is also provided. Also provided is a sample comprising a bound sensor provided by such a process. Also provided are kits useful for such methods.

3 Claims, 4 Drawing Sheets

DETECTION OF A TARGET IN A PRESERVATIVE SOLUTION

This application is a continuation of U.S application Ser. No. 10/618,443, filed Jul. 11, 2003 now abandoned; which is a continuation-in-part of U.S application Ser. No. 09/825,482, filed Apr. 3, 2001 now abandoned; which claims priority from Provisional Application 60/225,524, filed Aug. 15, 2000 and claims priority from Provisional Application 60/194,304, filed Apr. 3, 2000.

TECHNICAL FIELD

This invention relates to methods, articles and compositions useful in detecting target substances in an alcoholic preservative solution, and for identifying sensors useful for binding to such targets.

BACKGROUND OF THE INVENTION

Medical diagnostic testing methods are critical screening tools for the early detection of pathological conditions. Early detection permits the identification of such conditions at a stage when successful treatment is more likely. Early treatment also frequently involves less damaging or less invasive treatment methods and decreases the impact on the patient. In addition to routine screening, diagnostic testing is also used in a variety of other applications, including biopsy analysis and monitoring the results of ongoing medical treatment.

Typical methods of analyzing samples such as medical samples for the presence of particular components can include multiple processing steps such as fixation, staining, permeabilization, in situ hybridization, and other enzymatic and/or chemical treatments, depending on the particular assays being performed.

Limitations on the amount of diagnostic information that can be obtained from a sample include the size of the sample that can be obtained and readily manipulated, the processing time required to perform multiple tests, the tolerance of the sample for multiple treatment steps without loss of signal, and the cost for performing multiple methods of analysis.

Medical samples are frequently stained using a variety of techniques known in the art. A number of staining solutions include a fixative such as an alcohol, although many also require fixation steps. Often it is desirable to obtain additional information on a variety of species which are or may be present in the sample, and/or to obtain information about smaller components such as viruses or other cellular or other species which may occur in a sample but which cannot be adequately interrogated using staining methods.

Use of more precise molecular techniques such as in situ hybridization can provide even more detailed information from a sample than staining techniques. However, in situ hybridization requires multiple tedious manipulations of a sample, involving fixation, transfer to a slide, stepwise manipulations through solution gradients, coverslipping, lengthy hybridization steps, washing, drying and other processing steps. Such methods are time consuming and require exacting care at multiple steps.

There is a need in the art for improved procedures for analyzing samples, and for compositions and articles of manufacture useful in such methods.

SUMMARY OF THE INVENTION

This invention relates to methods, articles and compositions useful in detecting target substances in an alcoholic preservative solution, and for identifying sensors useful for binding to such targets. The methods allow for the simultaneous performance of sufficient fixation of a sample and binding of a detectable sensor to a target of interest in the sample. In one aspect, a method is provided that comprises contacting a sample suspected of containing a target with a detectable sensor molecule known to bind to such target in an alcoholic preservative solution. The method maybe performed in multiplex form to permit simultaneous analysis of a plurality of targets. Methods for identifying a sensor capable of binding to a desired target in an alcoholic preservative solution are also provided. An alcoholic preservative solution comprising one or more such detectable sensors is also provided. Also provided is a sample comprising a bound sensor provided by such a process. Also provided are kits useful for such methods.

BRIEF DESCRIPTION OF THE DRAWINGS

The patent or application file contains at least one drawing executed in color. Copies of this patent or patent application publication with color drawings will be provided by the Patent and Trademark Office upon request and payment of the necessary fee.

DETAILED DESCRIPTION OF THE INVENTION

Figure 1:
FIG. 1 shows an image of an *S. epidermitis* specimen negative for *S. aureus* hybridized with a fluorescein isothiocyanate(FITC)-labeled PNA probe specific for *S. aureus* rRNA after a 90 minute hybridization in PreservCyt solution, viewed with a 50× oil immersion lens and an Omega FITC/Texas Red dual filter.
Figure 2:
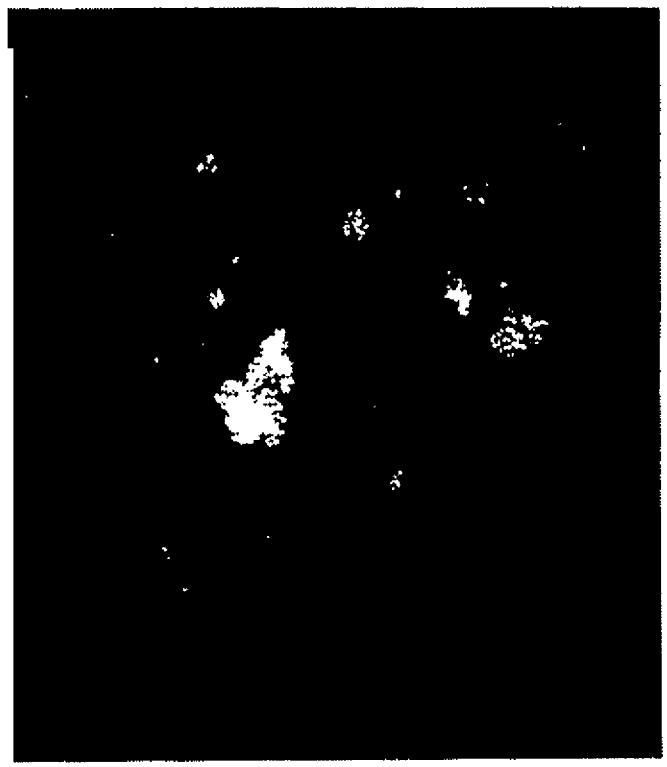
FIG. 2 shows an image of an *S. aureus*-positive specimen hybridized with a FTIC-labeled PNA probe specific for *S. aureus* rRNA after a 90 minute hybridization in PreservCyt solution, viewed with a 50× oil immersion lens and an Omega FITC/Texas Red dual filter.
Figure 2:
Figure 3:
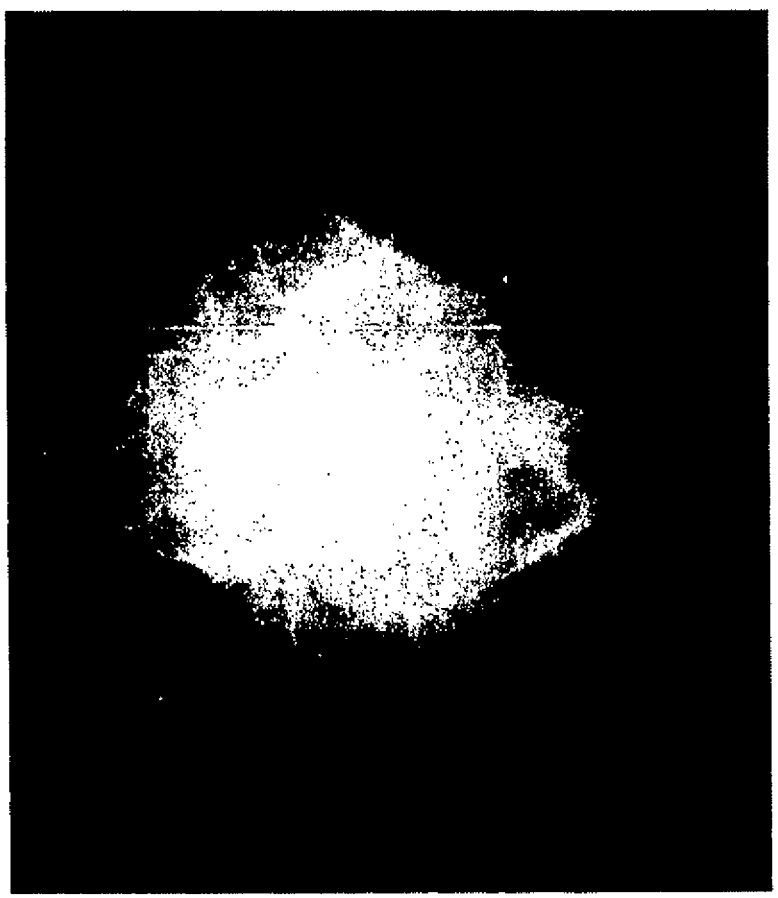
FIG. 3 shows an image of a yeast-negative ThinPrep-prepared sample hybridized with a FITC-labeled PNA probe specific for *C. albicans* rRNA viewed at 50× via oil immersion with an Omega dual filter.
Figure 4:
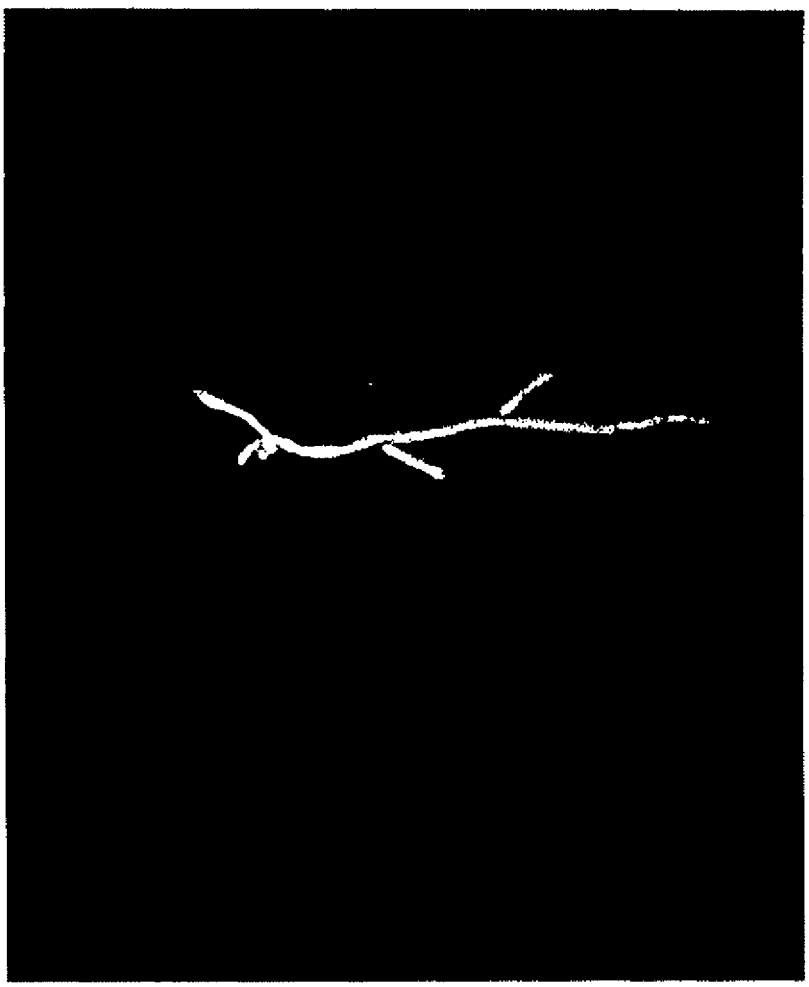
FIG. 4 shows an image of a yeast-positive ThinPrep-prepared sample hybridized with a FITC-labeled PNA probe specific for *C. albicans* rRNA, viewed with a 50× oil immersion lens and a FITC-/Texas Red dual filter. This ThinPrep specimen was collected in 1999 and hybridized after four years of storage in PreservCyt.

The inventors have advantageously discovered that incorporation of a sensor molecule into an alcohol-containing preservative solution allows for the performance of multiple cytological procedures in one solution, thereby decreasing the number of steps and the amount of time required to process a sample and increasing the number of assays which can be performed on a given sample in a given time period.

For example, a FISH procedure, which is cumbersome and requires multiple steps and manipulations, can be simplified if performed within an alcoholic preservative solution such as PreservCyt containing a sensor such as a PNA probe to detect the nucleic acid target. This advantageously eliminates the need for a time-consuming and unnecessary fixation step, because the methanol in PreservCyt can also act as a fixative.

We have performed studies demonstrating the utility of PNA probes for the microbial detection of *Staphylococcus aureus* and *Candida albicans* in PreservCyt® by FISH (fluorescent in situ hybridization). We have demonstrated that FISH with a PNA probe can be effectively performed within a solution matrix of PreservCyt. In the conventional method, the hybridization event is performed on a slide prepared from a blood culture specimen that needs to be fresh for optimal performance. Because of the preservative quality of PreservCyt, the stability of the PNA target (a rRNA sequence) is well maintained. Our studies show that rRNA integrity is sustained in PreservCyt and detectable by PNA FISH for at least four years. We have also determined that the hybridization event remains stable in PreservCyt at room temperature for at least 23 days. This advantageously provides for methods of retrospective analysis of previously obtained samples. Thus, detection methods for detecting a target after prolonged periods of storage in an alcoholic preservative solution are also provided. Methods of detecting a target may be performed after 1, 2 or 3 week, or after 1, 2, 3, 4, 6 or 9 months, or after 1, 2, 3, 4 or more years.

While the invention is exemplified by the detection of *C. albicans* and *S. aureus* by PNA FISH as a model system, it is not limited to methods of detecting these organisms. The methods can be applied to the detection of other infectious or pathologic agents (including viruses) as well as genetic analyses such as the identification of point mutations or other chromosomal abnormalities (i.e., centromere probes to detect aneuploidy).

The method can also be used for molecular assays in an alcoholic preservative solution, for example an amplification reaction, for example PCR, including the use of one or more PNA probes to block the amplification of undesirable targets, for example to detect particular selected strain(s) of Human Papilloma Virus (HPV), for example pathogenic strains, while avoiding the detection of other nonselected strain(s), for example nonpathogenic strains. The methods can be used in multiplex form. The methods can also be used to test candidate sensors for their ability to bind to a desired target; such testing may be done in multiplex form, for example using a library of compounds, for example small molecules, organic molecules, and/or inorganic molecules, or mixtures of test oligonucleotides for identifying an aptamer with a desired binding profile from a mixture.

The pathologic diagnosis of cancer generally requires the microscopic examination of single cells or tissue biopsy to identify morphologic abnormalities indicative of malignancy. Ancillary laboratory tests can augment morphologic examination. These tests include to the detection of: chromosomal abnormalities (e.g. amplification, deletion or translocation), abnormally expressed enzymes, proteins or lipids or carbohydrates. While different analytical methods may be used to demonstrate the abnormal cell component they share in common the notion that the analysis is performed on a group of cells, either in tissue section, fluid suspension or microscope slide that is different from the cells used in the initial morphologic examination. This can create a challenge for the diagnostic process.

The methods described herein maybe used to analyze the centrosomes present in a sample by using a centrosome-specific sensor. Currently, the enumeration of centrosomes is not practiced for the diagnostic adjunct for malignancy or its precursors. In one variation, a method for concurrent assessment for cell morphology and enumeration of centrosome numbers is provided so that, by combining information regarding both elements, a more accurate classification of normality versus abnormality can be determined. For example, a ThinPrep slide can be prepared from preserved cells and subjected to a Papanicolaou stain procedure. The cells can be contacted with a detectable sensor specific for a centrosomal target either before or after the staining procedure. The slide is examined by a specific, defined, wavelengths of light for the determination of morphologic features and specific binding of the centrosomal-specific sensor. An automated imaging system, for example the ThinPrep® Imaging System, can be employed to quantify the number of centrosomes by virtue of the binding the detectable sensor.

After exposure to the sensor in the preservative solution, the sample can be interrogated to determine whether the sensor has bound to the target. Interrogation may take place in a receptacle containing the sample in solution, or may be performed after transfer of some or all of the sample to a different vessel or to a substrate, for example a filter, slide, or coverslip. The sample can be interrogated with one or more specific, defined wavelengths of light for the determination of morphologic features and specific binding of the target and the presence of the sensor.

The sample(s) can be analyzed manually and/or by a suitable apparatus, for example an automated imaging system. Exemplary automated imaging systems include Cytyc Corporation's ThinPrep® Imaging System, the TriPath FocalPoint™ Profiler, the ChromaVision Acis® System, the CompuCyt iCyte Imaging System, the Applied Imaging CytoVision™ System, and the Veracel Verasys Imaging System. An apparatus such as these can be modified to incorporate one or more detection systems for the additional label(s) used on the sensors to be incorporated into the alcoholic preservative staining solution. For example, an apparatus may be adapted to detect and/or analyze one or more particular wavelengths provided by the sensor(s) (and/or their label(s)) added to the preservative solution. Where the target is a centrosome, an automated imaging system can be employed to quantify the number of centrosomes by detecting the amount or number of centrosome-specific sensors bound to the sample.

Before the invention is described in further detail, it is to be understood that this invention is not limited to the particular methodology, solutions or apparatuses described, as such methods, solutions or apparatuses can, of course, vary. It is also to be understood that the terminology used herein is for the purpose of describing particular embodiments only, and is not intended to limit the scope of the invention.

Use of the singular forms "a," "an," and "the" include plural references unless the context clearly dictates otherwise. Thus, for example, reference to "a sample" includes a plurality of samples, reference to "a sensor" includes a plurality of such sensors, reference to "a target" includes a plurality of targets, and the like. Additionally, use of specific plural references, such as "two," "three," etc., read on larger numbers of the same subject unless the context clearly dictates otherwise.

Terms such as "connected," "attached," and "linked" are used interchangeably herein and encompass direct as well as indirect connection, attachment, linkage or conjugation unless the context clearly dictates otherwise. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention, as are ranges based thereon. Where a combination is disclosed, each subcombination of the elements of that combination is also specifically disclosed and is within the scope of the invention. Conversely, where different elements or groups of elements are disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Unless defined otherwise or the context clearly dictates otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. These terms refer only to the primary structure of the molecule. Thus, the terms includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide.

Suitable hybridization conditions for a given assay format can be determined by one of skill in the art; nonlimiting parameters which may be adjusted include concentrations of assay components, pH salts used and their concentration, ionic strength, temperature, etc.

More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, h A, and mRNA, whether spliced or unspliced, any other type of polynucleotide which is an N- or C-glycoside of a purine or pyrimidine base, and other polymers containing alternative backbones, including peptide nucleic acid (PNA), and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms are used interchangeably herein. These terms refer only to the primary structure of the molecule. Thus, these terms include, for example, 3'-1-deoxy-2',5'-DNA, oligodeoxyribonucleotide N3'P5' phosphoramidates, 2'-O-alkyl-substituted RNA, double- and single-stranded DNA, as well as double- and single-stranded RNA, and hybrids thereof including for example hybrids between DNA and/or RNA and/or PNA and/or other forms, and also include known types of modifications, for example, labels, alkylation, "caps," substitution of one or more of the nucleotides with an analog, internucleotide modifications such as, for example, those with negatively charged linkages (e.g., phosphorothioates, phosphorodithioates, etc.), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

Furthermore, modifications to nucleotidic units include rearranging, appending, substituting for or otherwise altering functional groups on the purine or pyrimidine base which form hydrogen bonds to a respective complementary pyrimidine or purine. The resultant modified nucleotidic unit optionally may form a base pair with other such modified nucleotidic units but not with A, T, C, G or U. Abasic sites may be incorporated which do not prevent the function of the polynucleotide; preferably the polynucleotide does not comprise abasic sites. Some or all of the residues in the polynucleotide can optionally be modified in one or more ways.

Exemplary modified nucleotidic units include aziridinylcytosine, 4-acetylcytosine, 5-fluorouracil, 5-bromouracil, 5-carboxymethylaminomethyl-2-thiouracil, 5-carboxymethylaminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5-methoxyuracil, 2-methylthio-N-6-isopentenyladenine, uracil-5-oxyacetic acid methylester, pseudouracil, queosine, 2-thiocytosine, 5-methyl-2-thiouracil, 2-thiouracil, 4-thiouracil, 5-methyluracil, uracil-5-oxyacetic acid, 2,6-diaminopurine, and "locked" nucleic acid units (LNA) and an analog thereof. Koshkin, et al., Tetrahedron Letters 1998 39:4381-4384; PCT Publ. No. WO99/14226.

Standard A-T and G-C base pairs form under conditions which allow the formation of hydrogen bonds between the N3-H and C4-oxy of thymidine and the N1 and C6-NH2, respectively, of adenosine and between the C2-oxy, N3 and C4-NH2, of cytidine and the C2-NH2, N'-H and C6-oxy, respectively, of guanosine. Thus, for example, guanosine (2-amino-6-oxy-9-β-D-ribofuranosyl-purine) maybe modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine) results in a modified nucleotide which will not effectively base pair with guanosine but will form a base pair with isoguanosine. Isocytosine is available from Sigma Chemical Co. (St. Louis, Mo.); isocytidine maybe prepared by the method described by Switzer et al. (1993) Biochemistry 32:10489-10496 and references cited therein; 2'-deoxy-5-methyl-isocytidine may be prepared by the method of Tor et A, (1993) J. Am. Chem. Soc. 115:4461-4467 and references cited therein; and isoguamine nucleotides may be prepared using the method described by Switzer et al. (1993), supra, and Mantsch et al. (1993) Biochem. 14:5593-5601, or by the method described in U.S. Pat. No. 5,780,610 to Collins et al. Other nonnatural base pairs may be synthesized by the method described in Piccirilli et al. (1990) Nature 343:33-37 for the synthesis of 2,6-diaminopyrimidine and its complement (1-methylpyrazolo-[4,3]pyrimidine-5,7-(4H,6H)-dione). Other such modified nucleotidic units which form unique base pairs are known, such as those described in Leach et al. (1992) J. Am. Chem. Soc. 114:3675-3683 and Switzer et al., supra.

"Complementary" or "substantially complementary" refers to the ability to hybridize or base pair between nucleotides or nucleic acids, such as, for instance, between a sensor peptide nucleic acid and a target polynucleotide. Complementary nucleotides are, generally, A and T (or A and U), or C and G. Two single-stranded polynucleotides or PNAs are said to be substantially complementary when the bases of one strand, optimally aligned and compared and with appropriate insertions or deletions, pair with at least about 80% of the bases of the other strand, usually at least about 90% to 95%, and more preferably from about 98 to 100%.

Alternatively, substantial complementarity exists when a polynucleotide or PNA will hybridize under selective hybridization conditions to its complement. Typically, selective hybridization will occur when there is at least about 65% complementary over a stretch of at least 14 to 25 bases, preferably at least about 75%, more preferably at least about 90% complementary. See, M. Kanehisa Nucleic Acids Res. 12:203 (1984).

"Preferential binding" or "preferential hybridization" refers to the increased propensity of one polynucleotide or PNA to bind to its complement in a sample as compared to a noncomplementary polymer in the sample.

Hybridization conditions will typically include salt concentrations of less than about 1M, more usually less than about 500 mM and preferably less than about 200 mM. In the case of hybridization between a peptide nucleic acid or other similar nucleic acid and a polynucleotide, the hybridization can be done in solutions containing little or no salt. Hybridization temperatures can be as low as 5° C., but are typically greater than 22° C., more typically greater than about 30° C., and preferably in excess of about 37° C. Longer fragments may require higher hybridization temperatures for specific hybridization. Other factors may affect the stringency of hybridization, including base composition and length of the complementary strands, presence of organic solvents and extent of base mismatching, and the combination of parameters used is more important than the absolute measure of anyone alone. Other hybridization conditions which may be controlled include buffer type and concentration, solution pH, presence and concentration of blocking reagents to decrease background binding such as repeat sequences or blocking protein solutions, detergent type(s) and concentrations, molecules such as polymers which increase the relative concentration of the polynucleotides, metal ion(s) and their concentration(s), chelator(s) and their concentrations, and other conditions known in the art.

The terms "aptamer" (or "nucleic acid antibody") is used herein to refer to a single- or double-stranded polynucleotide that recognizes and binds to a desired target molecule by virtue of its shape. See, e.g., PCT Publication Nos. WO 92/14843, WO 91/19813, and WO 92/05285.

"Polypeptide" and "protein" are used interchangeably herein and include a molecular chain of amino acids linked through peptide bonds. The terms do not refer to a specific length of the product. Thus, "peptides," "oligopeptides," and "proteins" are included within the definition of polypeptide. The terms include polypeptides contain [post-translational] modifications of the polypeptide, for example, glycosylations, acetylations, phosphorylations, and sulphations. In addition, protein fragments, analogs (including amino acids not encoded by the genetic code, e.g. homocysteine, ornithine, D-amino acids, and creatine), natural or artificial mutants or variants or combinations thereof, fusion proteins, derivatized residues (e.g. alkylation of amine groups, acetylations or esterifications of carboxyl groups) and the like are included within the meaning of polypeptide.

As used herein, the term "binding pair" refers to first and second molecules that bind specifically to each other with greater affinity than to other components in the sample. The binding between the members of the binding pair is typically noncovalent. Exemplary binding pairs include immunological binding pairs (e.g. any haptenic or antigenic compound in combination with a corresponding antibody or binding portion or fragment thereof, for example digoxigenin and anti-digoxigenin, fluorescein and anti-fluorescein, dinitrophenol and anti-dinitrophenol, bromodeoxyuridine and anti-bromodeoxyuridine, mouse immunoglobulin and goat anti-mouse immunoglobulin) and nonimmunological binding pairs (e.g., biotin-avidin, biotin-streptavidin, hormone [e.g., thyroxine and corisol]-hormone binding protein, receptor-receptor agonist or antagonist (e.g., acetylcholine receptor-acetylcholine or an analog thereof. IgG-protein A, lectin-carbohydrate, enzyme-enzyme cofactor, enzyme-enzyme-inhibitor, and complementary polynucleotide pairs capable of forming nucleic acid duplexes) and the like. One or both member of the binding pair can be conjugated to additional molecules.

The term "antibody" as used herein includes antibodies obtained from both polyclonal and monoclonal preparations, as well as: hybrid (chimeric) antibody molecules (see, for example, Winter et al. (1991) Nature 349:293-299; and U.S. Pat. No. 4,816,567); F(ab')2 and F(ab) fragments; Fv molecules (noncovalent heterodimers, see, for example, Inbar et al. (1972) Proc Natl Acad Sci USA 69:2659-2662; and Ehrlich et al. (1980) Biochem 19:4091-4096); single-chain Fv molecules (sFv) (see, for example, Huston et al. (1988) Proc Natl Acad Sci USA 85:5879-5883); dimeric and trimeric antibody fragment constructs; minibodies (see, e.g., Pack et al. (1992) Biochem 31:1579-1584; Cumber et al. (1992) J Immunology 149B:120-126); humanized antibody molecules (see, for example, Riechmann et al. (1988) Nature 332:323-327; Verhoeyan et al. (1988) Science 239:1534-1536; and U.K. Patent Publication No. GB 2,276,169, published 21 Sep. 1994); and, any functional fragments obtained from such molecules, wherein such fragments retain specific-binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. Thus, the term encompasses antibodies obtained from murine hybridomas, as well as human monoclonal antibodies obtained using human hybridomas or from murine hybridomas made from mice expression human immunoglobulin chain genes or portions thereof. See, e.g., Cote, et al. Monoclonal Antibodies and Cancer Therapy, Alan R. Liss, 1985, p. 77.

"Muliplexing" herein refers to an assay or other analytical method in which multiple analytes can be assayed simultaneously.

"Optional" or "optionally" means that the subsequently described event or circumstance may or may not occur, and that the description includes instances where the event or circumstance occurs and instances in which it does not.

The Sample

The portion of the sample to be analyzed can be any source of biological material that can be obtained from a living organism directly or indirectly, including cells, tissue or fluid. Nonlimiting examples of the sample include blood, urine, semen, milk, sputum, mucus, plueral fluid, pelvic fluid, sinovial fluid, ascites fluid, body cavity washes, eye brushing, skin scrapings, a buccal swab, a vaginal swab, a pap smear, a rectal swab, an aspirate, a needle biopsy, a section of tissue obtained for example by surgery or autopsy, plasma, serum, spinal fluid, lymph fluid, the external secretions of the skin, respiratory, intestinal, and genitourinary tracts, tears, saliva, tumors, organs, a microbial culture, a virus, and samples of in vitro cell culture constituents.

The sample can be a positive control sample which is known to contain the target. A negative control sample can also be used which is used to determine whether a given set of conditions produces false positives.

The sample may be provided in solution or on a substrate as described below. The sample may be transferred to a substrate before or after the sample is contacted with the sensor molecule in the preservative solution.

The Substrate

The substrate can comprise a wide range of material, either biological, nonbiological, organic, inorganic, or a combination of any of these. For example, the substrate may be a polymerized Langmuir Blodgett film, functionalized glass, Si, Ge, GaAs, GaP, SiO2, SiN4, modified silicon, or any one of a wide variety of gels or polymers such as (poly)tetrafluoroethylene, (poly)vinylidenedifluoride, polystyrene, cross-linked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers, epoxies, polycarbonate, or combinations thereof.

Substrates can be planar crystalline substrates such as silica based substrates (e.g. glass, quartz, or the like), or crystalline substrates used in, e.g., the semiconductor and microprocessor industries, such as silicon, gallium arsenide and the like.

Silica aerogels can also be used as substrates, and can be prepared by methods known in the art. Aerogel substrates maybe used as free standing substrates or as a surface coating for another substrate material.

The substrate can take any form and typically is a plate, slide, coverslip, bead, pellet, disk, particle, strand, precipitate, membrane, optionally porous gel, sheets, tube, sphere, container, capillary, pad, slice, film, chip, multiwell plate or dish, optical fiber, etc. Although typically the substrate takes an inanimate form, for some applications the substrate can be any form that is rigid or semi-rigid.

Surfaces on the substrate can be composed of the same material as the substrate or can be made from a different material, and can be coupled to the substrate by chemical or physical means. Such coupled surfaces may be composed of any of a wide variety of materials, for example, polymers, plastics, resins, polysaccharides, silica or silica-based materials, carbon, metals, inorganic glasses, membranes, or any of the above-listed substrate materials. In one embodiment, the surface will be optically transparent and will have surface Si—OH functionalities, such as those found on silica surfaces.

The Target

The target may be any component of the sample that is desired to be visualized. Non limiting examples of the target include a polynucleotide, a protein, a polysaccharide, mucopolysaccharide, proteoglycan, lipid, cell, cell type, organism, virus, structure, or molecule to which a sensor can be obtained. The target may be a subcellular structure, for example a centrosome or centrosomal component, or an extracellular product or component.

Where the target is a cell or cell component or product, the cell can be of any origin, including prokaryotic, eukaryotic, or archea, The cell maybe living or dead. If obtained from a multicellular organism, the cell may be of any cell type. The cell may be a cultured cell line or a primary isolate, the cell maybe mammalian, amphibian, reptilian, plant, yeast, bacterium, spirochetes, or protozoan. The cell may be human, murine, rat, hamster, chicken, quail, or dog. The cell may be a normal cell, a mutated cell, a genetically manipulated cell, a tumor cell, etc.

Exemplary cell types from multicellular organisms include acidophils, acinar cells, pinealocytes, adipocytes, ameloblasts, astrocytes, basal (stem) cells, basophils, hepatocytes, neurons, bulging surface cells, C cells, cardiac muscle cells, centroacinar cells, chief cells, chondrocytes, Clara cells, columnar epithelial cells, corpus luteal cells, decidual cells, dendrites, endrocrine cells, endothelial cells, enteroendocrine cells, eosinophils, erythrocytes, extraglomerular mesangial cells, fetal fibroblasts, fetal red blood cells, fibroblasts, follicular cells, ganglion cells, giant Betz cells, goblet cells, hair cells, inner hair cells, type I hair cells, hepatocytes, endothelial cells, Leydig cells, lipocytes, liver parenchymal cells, lymphocytes, lysozyme secreting cells, macrophages, mast cells, megakaryocytes, melanocytes, mesangial cells, monocytes, myoepithelial cells, myoid cells, neck mucous cells, nerve cells, neutrophils, oligodendrocytes, oocytes, osteoblasts, osteochondroclasts, osteoclasts, osteocytes, pillar cells, sulcal cells, parathyroid cells, parietal cells, pepsinogen-secreting cells, pericytes, pinealocytes, pituicytes, plasma cells, platelets, podocytes, spermatocytes, Purkinje cells, pyramidal cells, red blood cells, reticulocytes, Schwann cells, Sertoli cells, columnar cells, skeletal muscle cells, smooth muscle cells, somatostatin cells, enteroendocrine cells, spermatids, spermatogonias, spermatozoas, stellate cells, supporting Deiter cells, support Hansen cells, surface cells, surface epithelial cells, surface mucous cells, sweat gland cells, T lymphocytes, theca lutein cells, thymocytes, thymus epithelial cell, thyroid cells, transitional epithelial cells, type I pneumonocytes, and type II pneumonocytes.

Exemplary types of tumor cells include adenomas, carcinomas, adenocarcinomas, fibroadenomas, ameloblastomas, astrocytomas, mesotheliomas, cholangiocarcinomas, cholangiofibromas, cholangiomas, chondromas, chondrosarcomas, chordomas, choriocarcinomas, craniopharyngiomas, cystadenocarcinomas, cystadenomas, dysgerminomas, ependymomas, epitheliomas, erythroid leukemias, fibroadenomas, fibromas, fibrosarcomas, gangliogliomas, ganglioneuromas, ganglioneuroblastomas, gliomas, granulocytic leukemias, hemangiomas, hemangiopericytomas, hemangiosarcomas, hibernomas, histiocytomas, keratoacanthomas, leiomyomas, leiomyosarcomas, lipomas, liposarcomas, luteomas, lymphangiomas, lymphangiosarcomas, lymphomas, medulloblastomas, melanomas, meningiomas, mesotheliomas, myelolipomas, nephroblastomas, neuroblastomas, neuromyoblastomas, odontomas, oligodendrogliomas, osteochondromas, osteomas, osteosarcomas, papillomas, paragangliomas, pheochromocytomas, pinealomas, pituicytomas, retinoblastomas, rhabdomyosarcomas, sarcomas, schwannomas, seminomas, teratomas, thecomas and thymomas.

Exemplary bacteria include *Staphylococcus aureus, Legionella pneumophila, Escherichia coli, M. tuberculosis, S. typhimurium, Vibrio cholera, Clostridium perfingens, Clostridium tetani, Clostridium botulinum, Clostridium baratii, Clostridium difficile, M. leprae, Helicobacter pylori, Hemophilus influenzae type b, Corynebacterium diphtheriae, Cornyebacterium minutissimum, Bordetella pertussis, Streptococcus pneumonia, Neisseria gonorrhoeae, Neisseria meningitides, Shigella dysenteriae, Pseudomonas aeruginosa, Bacteroides fragilis, Prevotella melaninogenica, Fusobacterium, Erysipelothrix rhusiopathiae, Listeria monocytogenes, Bacillus anthracis, Hemophilus ducreyi, Francisella tularensis, Yersinia pestis, Bartonella henselae, Klebsiella, Enterobacter, Serratia, Proteus*, and *Shigella*.

Exemplary spirochetes include *Treponema pallidum, T. pertenue, T. carateum, Borrelia recurrentis, B. vincentii, B. burgdorferi*, and *Leptospira icterohaemorrhagiae*.

Exemplary fungi include *Actinomyces bovis, Aspergillus fumigatus, Blastomyces dermatitidis, Candida albicans, Coccidioides immitis, Cryptococcus enoformans, Histoplasma capsulatum, Sporotrichum schenckii, Actinomyces israelii, Actinomyces bovis, Aspergillus fumigatus, Blastomyces dermatitidis, Candida albicans, Coccidioides immitis, Cryptococcus neoformans, Histoplasma capsulatum, Nocardia asteroides, Pneumocystis carinii, Sporothrix schenckii, Pichia pastoris, Saccharomyces cerevisiae*, and *Schizosaccharomyces pombe*.

Exemplary protozoa and parasites which maybe encoded include *Plasmodium falciparum, Entamoeba histolytica, trypansomes, Leishmania, Toxpolasma gondii, Giardia lamblia*, and *Chlamydia trachomatis*

Where the target is a polynucleotide, the target polynucleotide can be single-stranded, double-stranded, or higher order, and can take any topology, for example linear, circular, branched. Exemplary single-stranded target polynucleotides include mRNA, rRNA, tRNA, hnRNA, ssRNA or ssDNA viral genomes, although these polynucleotides may contain internally complementary sequences and significant secondary structure. Exemplary double-stranded target polynucleotides include genomic DNA, mitochondrial DNA, chloroplast DNA, dsRNA or dsDNA viral genomes, plasmids, phage, and viroids.

The Sensor

The sensor can be any substance which is stable and soluble and can selectively bind to its target in the alcohol-containing preservative solution. Nonlimiting examples of the sensor include a small organic chemical, an inorganic molecule, a polynucleotide as described above, including a peptide nucleic acid and an aptamer. Combinations of different sensors may also be used, which can allow for the detection and analysis of a plurality of targets in the sample. The sensor may be one chosen to bind specifically to a component of a cell, such as a centrosome or subcomponent thereof. A plurality of candidate sensor molecules, for example a library of chemicals, may be tested for binding to a desired target, which testing maybe done in the presence of the alcoholic preservative solution.

The sensor must be detectable, and maybe naturally detectable or may be rendered detectable by coupling to a label. Any effective detection method can be used, including optical, spectroscopic, electrical, piezoelectrical, magnetic, Raman scattering, surface plasmon resonance, radiographic, colorimetric, calorimetric, etc. Preferably the sensor is or can be rendered optically detectable to a human and/or a detection device. In one aspect, the detection is performed using a light-emitting diode (LED).

In one variation, the sensor may be a PNA that binds specifically to a target polynucleotide suspected of being present in the sample. PNA is a synthetic nucleic acid analog with a peptide-derived structure. It has a backbone composed of repeating N-2-aminoethyl glycine units linked by amide bonds instead of the sugar-phosphate groups found in DNA (1). PNA is frequently referred to as a "DNA mimic" as it obeys Watson-Crick base-pairing rules for hybridization to a complementary nucleic acid target (2). However, because of their peptide backbone, PNAs are neutrally charged and have unique properties superior to DNA, including increased thermal stability, rapid hybridization kinetics (50,000 times the rate of DNA:DNA hybridization) (3), and resistance to protease and nuclease degradation. Also, PNA can easily penetrate the cell wall of an organism to find its nucleic acid target because of its hydrophobic nature (4). These features make PNA an excellent tool for in-vitro diagnostics, specifically for in situ hybridization.

In another embodiment variation, the sensor may be an aptamer. Preparation of oligonucleotides which bind to a desired target has been described by Blackwell, T. K., et al., Science (1990) 250:1104-1110; Blackwell, T. K., et al., Science (1990) 250:1149-1152; Tuerk, G, and Gold, L., Science (1990) 249:505-510; Joyce, G. F., Gene (1989) 82:83-87; U.S. Pat. No. 5,270,163 to Gold et al. issued Dec. 14, 1993. Such oligonucleotides have been termed "aptamers." Tuerk and Gold describe the use of a procedure termed "systematic evolution of ligands by exponential enrichment." In this method, a pool of RNAs that are completely randomized at specific positions is subjected to selection for binding by a desired nucleic acid-binding protein which has been fixed on a nitrocellulose filter. The bound RNAs then are recovered and amplified as double-stranded DNA that is competent for subsequent in vitro transcription. The newly transcribed RNA then is recycled through this procedure to enrich for oligonucleotides that have consensus sequences for binding by the cognate protein. The oligonucleotides so obtained then may be sequenced for further study. Tuerk and Gold applied this procedure to identify RNA oligonucleotides which are bound by the RNA binding region of T4 DNA polymerase.

A sensor comprising an aptamer may be tested for binding in the presence of an alcoholic preservative solution such as PreservCyt, or maybe evolved in assays using such a solution. A sensor aptamer maybe prepared by any known method, including synthetic, recombinant, and purification methods, and may be used alone or in combination with other aptamers specific for the same target. The aptamer may be labeled and/or conjugated to other substances. The term "aptamer" specifically includes "secondary aptamers" containing a consensus sequence derived from comparing two or more known aptamers to a given target. Preparation of aptamers is extensively discussed in U.S. Pat. No. 5,582,981 to Toole et al. issued Dec. 10, 1996. The oligonucleotides used as starting materials to determine specific binding sequences for an aptamer sensor may be single-stranded or double-stranded DNA or NA, The starting material oligonucleotide will contain a randomized sequence portion, generally including from about 10 to 400 nucleotides, more preferably 20 to 100 nucleotides. The randomized sequence is flanked by primer sequences which permit the application of the polymerase chain reaction to the recovered oligonucleotide from the complex. Aptamers found to bind to the targets may be isolated, sequenced, and then resynthesized as conventional DNA or RNA moieties, or may be "modified" polynucleotides as described above. For example, any of the hydroxyl groups ordinarily present may be replaced by phosphonate groups, phosphate groups, protected by a standard protecting group, or activated to prepare additional linkages to additional nucleotides, or may be conjugated to solid supports. The 5' terminal OH is conventionally free but may be phosphorylated; OH substituents at the 3' terminus may also be phosphorylated. The hydroxyls may also be derivatized to standard protecting groups. One or more phosphodiester linkages may be replaced by alternative linking groups. These alternative linking groups include, but are not limited to embodiments wherein P(O)O is replaced by P(O)S, P(O)NR$_2$, P(O)R, P(O)OR', CO, or CNR$_2$, wherein R is H or alkyl (1-20C) and R' is alkyl (1-20C); in addition, this group may be attached to adjacent nucleotide through O or S, Not all linkages need to be identical. An aptamer may be determined for any desired target, for example a centrosomal component. A small molecule such as the crystallizing agents described in U.S. Pat. No. 6,368,818 to Kong issued Apr. 9, 2002, may also be used to bind to cellular organelles, including centrosomes, microtubules, and/or the cytoskeleton.

The process of cell division involves a series of controlled, interdependent biochemical reactions that first produce a copy of the chromosomes, followed by division of the cell. This process, termed mitosis, initially involves the formation of sub-cellular organelles that create the structural framework necessary for cell division. One important organelle is the centrosome, which, with its associated components, serves as an anchor point from which a network of microtubular proteins can separate the DNA of the parent from the daughter cell. The normal, resting cell typically has one centrosome, but prior to cell division there is centrosome duplication, so that two anchor points are formed. Cancer cells, or the precursor cells that lead to cancer may have an abnormal number of centrosomes. Thus, enumeration of centrosomes can be used to identify abnormal cells.

In one variation, a process to enumerate centrosomes is provided by contacting a sample with a centrosome-specific sensor incorporated into an alcoholic preservative solution, followed by quantitative imaging of a sample drawn from that mixture. Thus, a sensor may be used that preferentially binds to the centrosome, or the peri-centrosomal material, to allow the number of centrosomes to be counted by visual examination or by computer imaging. Exemplary centrosomal target molecules include katanin, a katanin subunit (see U.S. Pat. No. 6,429,304 to Vale et al. issued Aug. 6, 2002), eg5 (see U.S. Pat. No. 6,472,521 to Uhlmann et al. issued Oct. 29, 2002), Nlk1 (see U.S. Pat. No. 6,476,193), HSP90 (see U.S. Pat. No. 6,335,157 to Gonzalez et al. issued Jan. 1, 2002), a trinectin, pericentrin, cp140, centrin, γ-tubulin, α-tubulin, β-tubulin (see U.S. Pat. No. 5,972,626 to Doxsey issued Oct. 26, 1999), CENP-F (see U.S. Pat. No. 5,599,919 to Yen et al. issued Feb. 4, 1997), an aurora protein (see U.S. Pat. Nos. 6,207,401, 5,972,676 and 5,962,312), and BTAK (see U.S. Pat. No. 6,352,858). The terms "centrosome" and "centrosomal" and the like as used herein refer to both the peri-centrosomal as well as the centrosomal area; thus, for example, the term "centrosomal target" includes peri-centrosomal as well as centrosomal targets. The sensor may also include a detectable substrate for a centrosomal enzyme, which may be detectable upon binding and/or may produce a detectable reaction product when acted upon by the centrosomal enzyme.

Labels

Labels useful in the inventions described herein include any substance which can be detected, directly or indirectly, in association with target present in the sample upon binding of the sensor to the target. Exemplary labels include a chromophore, a lumiphore, a fluorophore, a chromogen, a hapten, an antigen, a radioactive isotope, a magnetic particle, a metal nanoparticle such as a gold or silver nanoparticle, an enzyme, an antibody or binding portion or equivalent thereof, an aptamer, and one member of a binding pair.

A fluorophore can be any substance which absorbs light of one wavelength and emits light of a different wavelength. Typical fluorophores include fluorescent dyes, semiconductor nanocrystals, lanthanide chelates, and a green fluorescent protein.

Exemplary fluorescent dyes include fluorescein, 6-FAM, rhodamine, Texas Red, tetramethylrhodamine, a carboxyrhodamine, carboxyrhodamine 6G, carboxyrhodol, carboxyrhodamine 110, Cascade Blue, Cascade Yellow, coumarin, Cy2®, Cy3®, Cy3.5®, Cy5®, Cy5.5®, Cy-Chrome, phycoerythrin, PerCP (peridinin chlorophyll-a Protein), PerCP-Cy5.5, JOE (6-carboxy-4',5'-dichloro-2',7'-dimethoxyfluorescein), NED, ROX (5- (and -6)-carboxy-X-rhodamine), HEX, Lucifer Yellow, Manna Blue, Oregon Green 488, Oregon Green 500, Oregon Green 514, Alexa Fluor® 350, Alexa Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-amino-4-methylcoumarin-3-acetic acid, BODIPY® FL, BODIPY® FL-Br$_2$, BODIPY® 530/550, BODIPY® 558/568, BODIPY® 564/570, BODIPY® 576/589, BODIPY® 581/591, BODIPY® 630/650, BODIPY® 650/665, BODIPY® R6G, BODIPY® TMR, BODIPY® TR, conjugates thereof, and combinations thereof. Exemplary lanthanide chelates include europium chelates, terbium chelates and samarium chelates.

A wide variety of fluorescent semiconductor nanocrystals ("SCNCs") are known in the art; methods of producing and utilizing semiconductor nanocrystals are described in: PCT Publ. No. WO 99/26299 published May 27, 1999, inventors Bawendi et al.; U.S. Pat. No. 5,990,479 issued Nov. 23, 1999 to Weiss et al.; and Bruchez et al., Science 281:2013, 1998. Semiconductor nanocrystals can be obtained with very narrow emission bands with well-defined peak emission wavelengths, allowing for a large number of different SCNCs to be used as signaling chromophores in the same assay, optionally in combination with other non-SCNC types of signaling chromophores.

The term "green fluorescent protein" refers to both native *Aequorea* green fluorescent protein and mutated versions that have been identified as exhibiting altered fluorescence characteristics, including altered excitation and emission maxima, as well as excitation and emission spectra of different shapes (Delagrave, S. et al. (1995) Bio/Technology 13:151-154; Heim, R et al. (1994) Proc. Natl. Acad. Sci. USA 91:12501-12504; Heim, R. et al. (1995) Nature 373: 663-664). Delgrave et al. isolated mutants of cloned *Aequorea victoria* GFP that had red-shifted excitation spectra. Bio/Technology 13:151-154 (1995). Heim, R. et al. reported a mutant (Tyr66 to His) having a blue fluorescence (Proc. Natl. Acad. Sci. (1994) USA 91:12501-12504).

Exemplary enzymes include those that are stable in an alcohol-containing preservative solution. Enzymes which may be tested for their stability under these conditions include alkaline phosphatase, horseradish peroxidase, β-galactosidase, glucose oxidase, a bacterial luciferase, an insect luciferase and sea pansy luciferase (*Renilla koellikeri*), which can create a detectable signal in the presence of suitable substrates and assay conditions, known in the art.

Exemplary haptens and/or members of a binding pair include avidin, streptavidin, digoxigenin, biotin, and those described above.

The Preservative Solution

The preservative solution is suitable for preservation of cells and tissue at ambient temperatures. The solution comprises an alcohol and preferably a buffer, and can be used for in vitro preservation of mammalian cells at ambient temperatures following biopsy, and prior to staining or other forms of analysis. The solution can be one such as described in U.S. Pat. No. 5,256,571 to Hurley et al. issued Oct. 26, 1993. In one embodiment, the preservation solution provides a medium for relatively long-term ambient preservation. In another embodiment, the preservation solution provides a medium for transportation and removal of undesired components, for example protein, from the sample solution.

More specifically, the preservative solution comprises a water-miscible alcohol, and preferably an anti-clumping agent and a buffering agent. The alcohol constituent is present in an amount sufficient to fix sample cells or tissue while still permitting acceptable binding of the sensor to its target. The alcohol is typically a lower alkyl ($C_{1-6}$) alcohol, and may be a $C_{1-4}$ alcohol, and may be selected from the group consisting of methanol, ethanol and isopropanol. In a preferred embodiment, the alcohol is methanol.

In one embodiment of the invention, the alcohol is present at a level sufficient for fixing and preserving the sample component of interest, and may be present in an amount greater than about 40% and less than about 60%, and may be about 45% or more, and may be about 55% or less. Solutions containing 60% or above of the alcohol constituent tend to exhibit clumping, or coagulation, which interferes with the subsequent ability to affectively stain the sample cells. Conversely, if the concentration of alcohol in this embodiment is at 40% or below, the cells are not sufficiently fixed for relatively long-term preservation, causing the cells to degrade over time. For this embodiment, the solution contains approximately 50% methanol, by solution.

In another embodiment of the invention, the alcohol is present in an amount of at least approximately 20 percent by solution. While this concentration of alcohol, as noted above, does not enable long-term preservation, (i.e., over two days), it does sufficiently fix cells for subsequent analysis within that time period. Alternatively, the cells maybe transferred from this 20% embodiment solution to a higher concentration of alcohol, for example 50%, for subsequent long-term preservation prior to analysis.

The anti-clumping agent may be present in an amount sufficient to prevent cells from clumping in solution. Any suitable anti-clumping agent effect in the alcoholic preservative solution can be used, and can be, for example, a chelating agent selected, for example, from the group consisting of ethylenediaminetetra-acetic acid (EDTA), and its salts, such as disodium, tripotassium and tetrasodium. Other agents deemed useful as the anti-clumping agent include cuminin, heparin, streptokinase, and such agents found in lysing or anticoagulant compositions.

Any buffering agent which can maintain the preservative solution at a desired pH during use may be used. Exemplary buffering agents include PBS, Tris, sodium acetate, and citric acid. EDTA and its salts may also be used as a buffering agent. The buffering agent is preferably one which maintains the pH of the solution within a range of between about four to about seven for the duration of preservation. Accordingly, a preferred buffer is an acetate buffer, such as sodium acetate, magnesium acetate, calcium acetate, and combinations thereof. White other buffers, such as phosphate or Tris buffers, may be used in the present solution, the effective buffering range of these buffers is deemed to be not as broad at the desired pH as that of acetate.

The buffer, particularly in long-term storage, used preferably has a large buffering range to accommodate any change in pH resulting from autolytic by-products from the sample cells suspended in the solution. For example, as cervical cells age, they release autolytic by-products that alter the pH balance of the suspension solution. In addition, the preservation of different cell types may require solutions of different acidity and within different pH ranges. Accordingly, a solution having a broad buffering range can be used for a wide range of cell types.

In one embodiment, the preservative solution comprises methanol, EDTA as acid, and sodium acetate. In that embodiment, the solution constitutes about 45-55 percent methanol, the EDTA constitutes about 2-4 percent, and the sodium acetate buffer constitutes about 6-8 percent.

In another embodiment, the preservative solution comprises methanol, a combination of sodium and potassium EDTA salts, and an acetate buffer. In a further embodiment, the solution comprises methanol, magnesium acetate, calcium acetate, potassium chloride, and sodium chloride in which the alcohol constitutes approximately 20 percent of the solution, about 0.1% sodium chloride, 10 mM potassium chloride, 2 mM calcium acetate, and 1 mM magnesium acetate.

The preservative solution is suitable for preserving suspended cells at an ambient temperature in the range of from about 4° to about 38° centigrade (C) for a period of at least approximately three weeks. Throughout this time, the cells retain sufficient structure to enable staining without a significant loss of integrity. The solution can enhance maintenance of the nuclear structure of the cells, in that it can maintain cell membranes sufficiently to allow subsequent cytological staining. The solution can also destroy microbial pathogens in a sample, and inhibit retroviral activity. The solution can remove undesired components such as protein from the sample.

This duration may be altered by both the stored age of the solution prior to ambient cell suspension, the amount of time between cell sampling and cell suspension, and the alcohol content. For example, if the solution has been stored for a significant length of time, in either a refrigerated state or an ambient state, then the remaining cell-preserving viability of the solution may be limited.

In addition to being a cell preservative, the solution can also kill selected pathogens. For example, in test samples the solution effectively kills the following organisms: *Candida albicans, Aspergillus niger, Escherichia coli, Pseudomonas aeruginosa*, and *Staphylococcus aureus*.

A detergent may be used in the solution. The detergent may be non-ionic, cationic, anionic or zwitterionic. Mixtures of detergents may also be used. Exemplary classes of detergents include alcohol ether sulfates, alcohol sulfates, alkanolamides, ally sulfonates, amine oxides, amphoteric detergents, anionic detergents, betaine derivatives, cationic detergents, disulfonates, dodecylbenzene sulfonic acid, ethoxylated alcohols, ethoxylated alkyl phenols, ethoxylated fatty acids, glycerol esters hydrotropes, lauryl sulfates, mono and diglycerides, non-ionic detergents, phosphate esters, quaternary detergents, and sorbitan derivatives.

Kits

Kits comprising reagents useful for performing the methods of the invention are also provided. In one embodiment, a kit comprises an alcoholic preservative solution and a detectable sensor suitable for binding to a centrosomal target in a sample when presented in the solution. The sensor may be conjugated to a label, which may be a chromophore, including a fluorophore.

The components of the kit may be retained by a housing. Instructions for using the kit to perform a method of the invention maybe provided with the kit, and can be provided in any fixed medium. The instructions maybe located inside the housing or outside the housing, and may be printed on the interior or exterior of any surface forming the housing which renders the instructions legible. The kit may be in multiplex form, containing pluralities of one or more different sensors which can bind to corresponding different targets in the sample.

EXAMPLES

The following examples are set forth so as to provide those of ordinary skill in the art with a complete description of how to make and use the present invention, and are not intended to limit the scope of what is regarded as the invention. Efforts have been made to ensure accuracy with respect to numbers used (e.g., amounts, temperature, etc.) but some experimental error and deviation should be accounted for. Unless otherwise indicated, parts are parts by weight, temperature is degree centigrade and pressure is at or near atmospheric, and all materials are commercially available.

Example 1

A volume of 50 ul of PNA is mixed into either a ThinPrep vial (Cytyc Corp.) or microfuge tube containing a volume of cellular PreservCyt (Cytyc Corp.) and the hybridization event takes place in solution using a 55° C. water bath. Alternatively, the hybridization event can be performed overnight at room temperature. Following hybridization, the specimen is centrifuged at 12,000 rpm for 5 min to pellet the cells then resuspended in a volume of wash buffer. The cells are washed by placing the sample in a 55° C. water bath for 30 minutes. Following washing, the sample is centrifuged again as previously described and resuspended in a new volume of wash buffer before transferring to a slide. The slide is air dried, coverslipped and reviewed for positivity (the presence of clusters of green fluorescing organisms in multiple fields of view). Alternatively, the specimen can also be washed by processing the specimen on a T2 processor to make the slide (the unbound probe is removed during the cell collection process of the T2 operation). Here, the prepared slide is released by the T2 processor into a collection vial of 1× Wash Buffer (AdvanDx) and then incubated within the buffer at 55° C. for 30 min.

Example 2

A method was developed to detect microorganisms in PreservCyt solution by FISH (fluorescent in-situ hybridization) using PNA technology.

The PNA probes used in these studies were obtained from AdvanDx, Inc. AdvanDx, Inc. produces PNA kits for *S. aureus* and *C. albicans* under license from Boston Probes, Inc. The intended use is the detection of *C. albicans* and *S. aureus* from smears prepared from blood cultures (for research use only).

Procedure for In-Solution Hybridization in PreservCyt:
1. Add 50 ul of PNA probe to 500 ul of PreservCyt specimen and vortex. Place in a 55° C. water bath (90 min. or overnight) to hybridize.
2. Process specimen on a T2 processor to transfer the cells onto a ThinPrep slide. After cell spot is prepared, instrument will release slide into a collection vial of 1× Wash Buffer (AdvanDx).
3. Incubate slide (submerged in the 1× Wash Buffer) in a 55° C. water bath for 30 min.
4. Remove slide and let air dry. Mount, coverslip, and view under fluorescent microscope. Positivity is determined by the presence of clusters of green fluorescing organisms in multiple fields of view ≠* Method was primarily performed using cellular PreservCyt spiked with *C. albicans* or *S. aureus*. However, the assay performance has also been demonstrated using *C. albicans* positive ThinPrep specimens that were up to four years old (slide-based).

Conventional Method (as Outlined in the AdvanDx kit Insert Sheet):
1. Place one drop of Fixation Solution (AdvanDx) on a microscope slide (AdvanDx), followed by one drop of blood culture specimen and mix.
2. Fix the smear by heating for 20 min. at 55-80° C.
3. Immerse slide in 80% or 96% ethanol for 5-10 min and air dry.
4. Place one drop of PNA probe onto the fixed smear, cover slip, and incubate at 55° C. for 90 min to hybridize.
5. Place slide in preheated 1× Wash Solution at 55° C. and remove coverslip. Incubate in the Wash Solution at 55° C. for 30 min.

Remove slide and let air dry. Mount, coverslip, and view under fluorescent microscope. Positivity is determined by the presence of clusters of green fluorescing organisms in multiple fields of view.

CONCLUSION

Performing in-solution hybridization in PreservCyt verifies the technique of adjunctive molecular testing out of the ThinPrep® vial. This demonstrates that a ThinPrep specimen containing a PNA probe can be processed on the ThinPrep® 2000 Processor after FISH without compromising the target to PNA hybridization event. Cells and target organism are both transferred to the slide, resulting in a monolayer of cells that is easier to interpret than the conventional smear method. Also, the ThinPrep processor facilitates the removal of unbound PNA from the sample, resulting in a prepared slide with less background noise. Performing the hybridization within the ThinPrep vial and preparing the slide on the ThinPrep Processor simplifies the FISH procedure by reducing the number of steps while streamlining the process for adjunctive molecular testing.

The invention claimed is:
1. A method for the detection of a target in a sample, wherein the target binds to one or more peptide nucleic acid (PNA) probe(s), the method comprising: contacting said sample with one or more PNA probe(s) in an aqueous alcohol solution of at least approximately 20% by volume solution under conditions in which the PNA probe(s) can bind to the target, if present; and detecting the PNA probe(s)

bound to the target, wherein the aqueous alcohol solution is at least approximately 40% by volume.

2. The method of claim 1, wherein the aqueous alcohol solution is at least approximately 50% by volume.

3. The method of claim 1, wherein the aqueous alcohol solution is greater than approximately 45% by volume and less than approximately 60% by volume.

\* \* \* \* \*